(12) United States Patent
Müller

(10) Patent No.: US 6,225,079 B1
(45) Date of Patent: May 1, 2001

(54) MICROTITRATION UNIT

(75) Inventor: Frank J. Müller, Schobüll (DE)

(73) Assignee: Gist-Brocades N.V. (NL)

( * ) Notice: Subject to any disclaimer, the term of this patent is extended or adjusted under 35 U.S.C. 154(b) by 0 days.

(21) Appl. No.: 08/401,077

(22) Filed: Mar. 8, 1995

Related U.S. Application Data

(63) Continuation of application No. 08/198,498, filed on Feb. 18, 1994, now abandoned.

(30) Foreign Application Priority Data

Feb. 19, 1993 (DE) .............................................. 93 02423 U

(51) Int. Cl.[7] ...................................................... C12Q 1/20
(52) U.S. Cl. ............................ 435/33; 435/29; 435/288.4
(58) Field of Search ................................. 435/30, 32, 33, 435/296, 297, 299–301, 288.4; 422/55, 58, 61, 74, 102; 436/22

(56) References Cited

U.S. PATENT DOCUMENTS

| | | | |
|---|---|---|---|
| 2,874,091 | * | 2/1959 | Fisk . |
| 3,126,325 | * | 3/1964 | Poole ..................................... 435/32 |
| 3,597,326 | * | 8/1971 | Liner . |
| 3,941,658 | * | 3/1976 | Lameris et al. ........................ 435/32 |
| 4,247,634 | * | 1/1981 | Abdou ................................... 435/33 |
| 4,255,522 | * | 3/1981 | Fusenig et al. . |
| 4,999,303 | * | 3/1991 | Jaeger et al. . |

* cited by examiner

Primary Examiner—Jan Ludlow
(74) Attorney, Agent, or Firm—Bierman, Muserlian and Lucas

(57) ABSTRACT

A microtitration unit being at least one container of transparent material for accommodating biological test reaction mixtures. The container is subdivided into at least two chambers suitable for accommodating different test reaction mixtures by at least one partition which extends from the inside of the bottom of the container and which is of lower height than the internal height of the container.

1 Claim, 1 Drawing Sheet

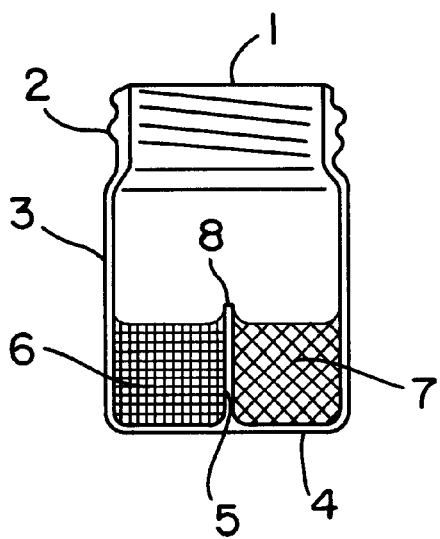
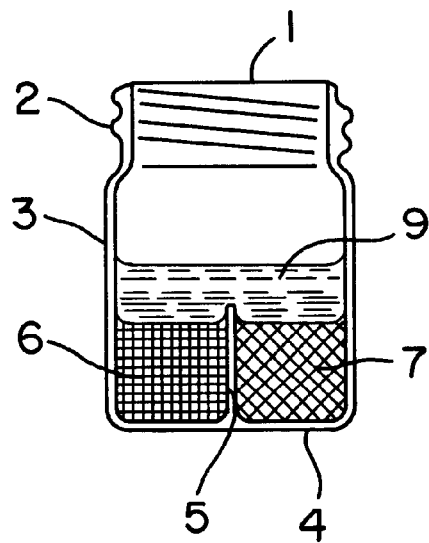
FIG. 1A  FIG. 1B
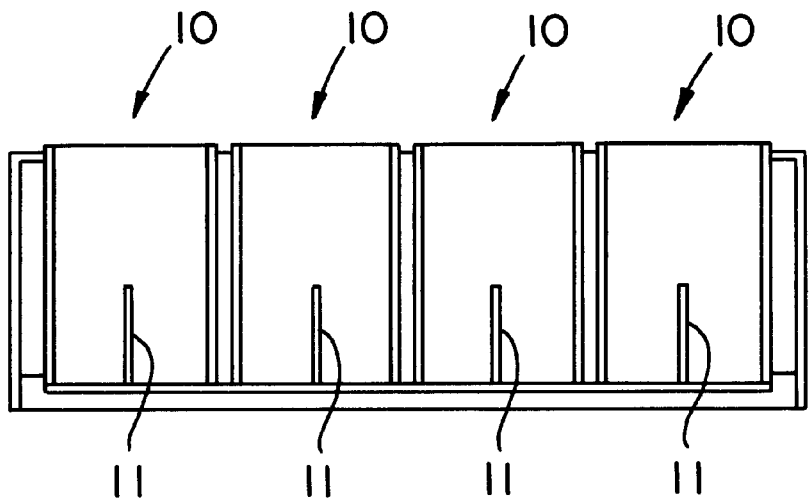
FIG. 2

MICROTITRATION UNIT

This application is a continuation of U.S. patent application Ser. No. 08/198,498 filed Feb. 18, 1994, now abandoned.

BACKGROUND OF THE INVENTION

One form of microtitration unit for testing and analysing for example biological fluids has at least one container of transparent material, for accommodating a biological test reaction mixture, with an opening for introducing the mixture.

Microtitration units of that kind which are often in the form of a plate having a plurality of containers arranged in juxtaposed relationship may be used for the routine investigation of biological fluids for medicament residues. The investigation essentially extends to the presence of antibiotics and sulfonamides. For that purpose the containers are partially filled with a biological test reaction mixture which is usually made up on the basis of agar-agar nutrient media and contains test micro-organisms and a color indicator. The biological fluid to be investigated, for example milk, is pipetted on to the biological test reaction mixture in the container. The container is then possibly closed and then incubated at the optimum temperature for the test micro-organisms in an incubation cabinet or in a water bath. During the incubation operation any medicament residue in the biological fluid to be investigated diffuse out of same into the test reaction mixture and impede metabolism of the test micro-organism. If metabolism occurs, there is a change in color of the color indicator, for example from blue to yellow whereas the presence of medicament residues is indicated by the absence of a change in color.

In order to be able to detect all possible medicament residues, tests are required, with at least two different test reaction mixtures, and that requires a plurality of test operations and is accordingly time-consuming and expensive.

SUMMARY OF THE INVENTION

An object of the present invention is to improve a microtitration unit in such a way that a sample can be subjected to tests in one working operation, using a plurality of different test reaction mixture.

Another object of the present invention is to provide a microtitration unit which affords simplicity of operation while giving reliable testing results.

In accordance with the invention the foregoing and other objects are attained by a microtitration unit comprising at least one container of transparent material. The container is subdivided into at least two chambers for accommodating different test reaction mixtures, by at least one partition which extends from the inside of the bottom of the container and which is of smaller height than the internal height of the container.

As will be seen in greater detail hereinafter in connection with preferred embodiments of the invention, a plurality of different test reaction mixtures can be introduced into the container of the microtitration unit or a plurality of containers where the unit has more than one container, more specifically preferably in such a way that the partition is allowed to project upwardly slightly above the respective filling levels of the different test reaction mixtures introduced into the container. When then the biological fluid to be tested is subsequently introduced for example by means of a pipette, the biological fluid floods over the different test chambers of the container if such an amount of biological test fluid is introduced by means of the pipette, that the test fluid also floods over the top edge of the partition. In a subsequent incubation operation any medicament residues which are possibly present can then diffuse out of the sample which has jointly introduced by means of the pipette for the different test reaction mixtures, into the respective test reaction mixtures, and possibly impede metabolism of the respective test micro-organism. The test reaction mixtures which are introduced into the individual chambers of a respective container are suitable for indicating different medicament residues so that as a result a test with a plurality of test reaction mixtures and accordingly optimum detection can be effected by one operation of introducing a fluid to be investigated, as by means of a pipette.

If there are no medicament residues in the biological fluid to be investigated, a change in color occurs in all chambers of the container. If the biological fluid to be investigated contains medicaments in relatively small amounts, it is possible that only the test reaction mixture in one chamber of the container reacts positively. That result can then give a clear indication of the nature of the medicament residue present.

Further objects, features and advantages of the invention will be apparent from the following description of preferred embodiments.

BRIEF DESCRIPTION OF THE DRAWING

FIG. 1A is a side view in section of a microtitration unit container according to the invention which has a screw closure, with two chambers and with test reaction mixtures disposed therein, FIG. 1B shows a container as shown in FIG. 1A, but further including a biological test fluid introduced into some by a pipette, and FIG. 2 is a diagrammatic view of a plurality of containers according to the invention which are arranged in juxtaposed relationship.

DESCRIPTION OF PREFERRED EMBODIMENTS

Referring firstly to FIGS. 1A and 1B a microtitration unit according to the invention comprises at least one container which comprises transparent material. The container has an opening 1 which is disposed at the top and which can be closed be means of a cover (not shown) which can be screwed on to a screwhead 2. The container which is of a round configuration in plan view has a wall 3 and a bottom 4. Extending from the inside of the bottom 4 upwardly in the container is a partition 5 whose height, as can be seen, is less than the internal height of the container. The partition 5 divides the container into two chambers in the illustrated embodiment. A test reaction mixture which is identified by reference 6 is introduced into the chamber shown on the left in FIGS. 1A and 1B while a test reaction mixture identified by references numeral 7 is introduced into the chamber shown on the right. The test reaction mixtures 6 and 7 are made up on the basis of agar-agar nutrient media and contain test micro-organisms as well as a color indicator. The test reaction mixtures 6 and 7 are of different compositions and are such that they are each suitable for indicating different medicament residues in biological fluids to be tested. The test reaction mixtures are introduced into the container to such a level that the top edge 8 of the partition 5 is allowed to project somewhat above the surface of the test reaction mixtures 6 and 7.

For carrying out the desired test, a biological fluid 9 to be investigated is introduced as by means of a pipette, more specifically in such an amount that the top edge 8 of the partition 5 is flooded over thereby. The filling level of the biological test fluid to be investigated (for example milk) is shown if FIG. 1B at an exaggerated height, for demonstration purposes.

It will be seen therefore that with the illustrated embodiment of FIGS. 1A and 1B a test can be carried out with the two different test reaction mixtures 6 and 7 with a single operation of introducing by means of a pipette a fluid to be investigated.

FIG. 2 shows a microtitration unit comprising an arrangement of a plurality of containers 10 which are each subdivided by an upwardly extending partition 11 into chambers which are suitable for accommodating different test reaction mixtures. Each partition 11 is lower in height than the internal height of the containers 10.

It will be appreciated that it is also possible in accordance with the invention for partitions to be so disposed in the or each container that they provide more than two chambers which are suitable for accommodating different test reaction mixtures.

It will be appreciated that the above-described embodiments of the invention have been set forth solely by way of example and illustration thereof and that various modifications and alterations may be made therein without thereby departing from the spirit and scope of the invention.

What is claimed is:

1. A method for testing and analyzing a biological test fluid comprising introducing into at least two chambers of a microtitration unit, different test reaction mixtures, comprising agar-agar nutrient medium, test microorganisms and a microbial growth indicator, said microtitration unit having at least one container of transparent material, the container including an opening for the introduction of test reaction mixtures and biological test fluid and at least one partition subdividing the container into said at least two chambers for accommodating said biological test reaction mixtures, the at least one partition extending from the inside of the container bottom and being of lower height than the internal height of the container and above the filling levels of the different test reaction mixtures, adding a sufficient amount of biological test fluid to be tested or analyzed whereby the biological test fluid flows over the top edge of the at least one partition whereby the biological test fluid floods over the at least two chambers and the biological test fluid makes contact with the different test reaction mixtures, and detecting the results of the interactions of the biological test fluid with the different test reaction mixtures.

\* \* \* \* \*